(12) United States Patent
Ryan (10) Patent No.: US 8,123,731 B2
(45) Date of Patent: Feb. 28, 2012

(54) METHOD AND APPARATUS FOR DISPOSING OF LIQUID SURGICAL WASTE FOR PROTECTION OF HEALTHCARE WORKERS

(75) Inventor: Marshall C. Ryan, Grantsburg, WI (US)

(73) Assignee: BioDrain Medical, Inc., Orono, MN (US)

( * ) Notice: Subject to any disclaimer, the term of this patent is extended or adjusted under 35 U.S.C. 154(b) by 357 days.

(21) Appl. No.: 12/277,985

(22) Filed: Nov. 25, 2008

(65) Prior Publication Data
US 2009/0076470 A1    Mar. 19, 2009

Related U.S. Application Data

(62) Division of application No. 10/524,086, filed as application No. PCT/US03/25018 on Aug. 8, 2003, now Pat. No. 7,469,727.

(60) Provisional application No. 60/405,000, filed on Aug. 21, 2002.

(51) Int. Cl.
*A61M 1/00* (2006.01)

(52) U.S. Cl. ........ 604/317; 604/318; 604/319; 604/326; 604/540; 604/541; 141/65; 141/83; 141/95

(58) Field of Classification Search .................. 604/317, 604/318, 319, 326, 540, 541; 141/65, 83, 141/95
See application file for complete search history.

(56) References Cited

U.S. PATENT DOCUMENTS

| | | | |
|---|---|---|---|
| 4,795,448 A | | 1/1989 | Stacey et al. |
| 5,091,863 A | * | 2/1992 | Hungerford et al. ........... 700/283 |
| 5,242,434 A | * | 9/1993 | Terry ............................ 604/317 |
| 5,741,238 A | * | 4/1998 | Bradbury et al. ............. 604/322 |
| 5,776,118 A | * | 7/1998 | Seifert et al. .................. 604/317 |
| 5,914,047 A | * | 6/1999 | Griffiths ........................ 210/739 |

* cited by examiner

*Primary Examiner* — Tatyana Zalukaeva
*Assistant Examiner* — Ginger T Chapman
(74) *Attorney, Agent, or Firm* — Larkin Hoffman Daly & Lindgren, Ltd.; Thomas J. Oppold (57) ABSTRACT

An improved method for measuring and automatically disposing of infectious waste generated during and after surgical and clinical procedures is provided. The infectious waste removal device includes a suction source, a method for pressure verification, separation chamber for isolating fluids, containment reservoir, measurement chamber for determining fluid received, an information source for such fluid volumes, a quantitative method for calculating fluid dynamics, a post use cleaning method, and other attributes for use by the surgical team or healthcare staff in order to minimize health care worker handling of said infectious waste and to limit their possible exposure.

11 Claims, 10 Drawing Sheets

METHOD AND APPARATUS FOR DISPOSING OF LIQUID SURGICAL WASTE FOR PROTECTION OF HEALTHCARE WORKERS

BACKGROUND OF THE INVENTION

1. Field of the Invention

The present invention relates to surgical procedures, and more particularly to a method and apparatus for the removal of liquid wastes generated during and after the course of said procedures.

2. Description of Related Art

The present invention relates to devices and methods for material handling, monitoring, and documentation for use in the medical field and in one embodiment a method and apparatus for handling, collecting, measuring and/or disposing of fluids, including gases and liquids, that are associated with surgical and other medical procedures. The use of the method and apparatus of the present invention will reduce the number of potential exposure events of healthcare workers to infectious and possibly toxic waste associated with surgery, clinical procedures, post-operative, and intensive care settings.

There has long been recognition of the collective potential for ill effects to healthcare workers from exposure to biohazardous materials in a variety of healthcare settings. Federal and state regulatory agencies have issued mandatory guidelines for the control of such materials, in particular blood-borne pathogens.

The presence of biohazardous materials is most common in surgical suites, clinical procedural settings, and intensive, and post-operative care units where body fluids, including blood and irrigation fluids, are removed from the patient during the procedure. Medical personnel may be exposed to these potentially serious biohazards during the course of their job performance, via direct contact of blood materials, or more indirectly, via splash and spray.

Current methods for the removal, containment, and disposal of high volume wastes containing these potentially hazardous materials pose the greatest risk of exposure to the healthcare team. For example, during the course of surgical and certain medical procedures, these fluids are continuously removed from the procedure site, via one or more end effectors operably coupled to wall suction via tubing. These fluids are suctioned into an end collection device and moved through tubing to a collection canister. In order to prevent them from entering a wall suction system where they would contaminate said system, the fluids are collected and stored, for the duration of the procedure, in large canisters (typically 1,500-3,000 cc capacity) positioned adjacent to the site of the procedure. These canisters are necessary to protect the integrity of the wall suction source and to assist the healthcare team in determining the hemostasis of the patient. Such canisters have graduated markings on them, allowing the healthcare team to make estimates of the volume of fluid loss from the patient during and following the procedure. The canisters are usually made of clear plastic material or glass and provide the healthcare team with qualitative, visual assessment by viewing the color of the fluids within the canister as an indicator of actual blood loss. The fluid contents are retained in the canisters adjacent to the procedure site until said procedure is completed, at which time post-operative assessment and documentation of fluids lost by the patient can be assessed.

During a surgical procedure, it is routine for the surgical team to estimate fluid loss using the measurement calibrations on the canister to roughly quantify fluid volumes removed from the site. These volumes are compared to known quantities of fluid introduced, e.g. sterile saline, which provides irrigation of tissue for enhanced visualization and prevention of tissue desiccation. After the procedure is completed, the removed fluids are measured and a calculation of total blood loss is determined. This is done to ensure no excess fluids of any type remain within the body cavity or that excessive blood loss has not occurred, both being circumstances that may place the patient at an increased post-operative risk.

Once total blood loss has been calculated, healthcare personnel must dispose of the fluids remaining in the canister(s). In one current method, this is done by removing the canister from the procedure site and transporting it to a disposal site within the facility. There, the top of the canister is manually opened and the contents are poured into a specially designated sink called a Hopper. The liquid waste is thus drained directly to the sanitary sewer, a process that exposes the healthcare worker to the most risk for direct contact or splash exposure. Once emptied, the canister(s) is placed in large, red pigmented, trash bags and disposed of as biohazardous waste—a process commonly referred to as "Red-Bagging." Alternatively, the canister(s) is opened in the operating room and a gel forming chemical powder is poured into each canister rendering the material gelatinous. These gelled canisters are then Red-Bagged and removed to a biohazardous holding area for disposal. In larger facilities, the canisters, whether pre-treated with gel or not, are often removed on large carts and transported to a separate biohazardous handling area where they are processed and prepared for disposal. Red-Bagged materials are disposed of separately from other medical and non-medical waste by companies specializing in that method of disposal.

Although these protection and disposal techniques are helpful and provide some measure of improvement over earlier methods, they fall short of providing adequate protection for healthcare personnel assigned to disposal of biohazardous waste. A major spill of fluid from said canister(s), whether by direct contact as a result of leakage or breakage, splash associated with the opening of the canister lid to add gel, while pouring liquid contents into the Hopper, or during the disposal process itself is cause for concern. Acute exposure to blood components is one of the most serious risks any healthcare worker faces in the performance of his or her job. Once a spill occurs, the entire area around the spill must be cleaned and disinfected and the exposed worker faces an uncertain future with regard to potential infection from bloodborne pathogens. These pathogens include, but are not limited to, HTV, HPV, and other infectious agents.

The present invention is well suited for use in the medical field, particularly in surgery, clinical settings, intensive and post-operative care units, whether such procedures and care are being carried out in an operating room or other clinical locations. It provides for the removal and disposal of certain fluids and liquids which are associated with medical procedures and protocols, and provides for assessing or measuring the quantity of and other essential characteristics of such liquids, e.g. saline solution, blood, plasma, ascites and the like, produced or used during said procedures or protocols. In addition, the present invention is well suited for use in many other markets, including but not limited to, veterinary medicine, research facilities, manufacturing and industrial applications, coroner and mortuary procedures, and food processing applications.

SUMMARY

The present invention will reduce healthcare personnel's contact and potential for exposure to potentially infectious liquid waste generated by medical procedures by providing a "no-touch" method of fluid and liquid management for use by healthcare workers.

In one embodiment of the present invention, a vacuum system, suitable for collecting medical procedure waste is operably coupled to one or more end effectors. The connector employed facilitates the coupling of the effectors to tubing and is adapted to receive liquid and/or gaseous material. The system collects and measures the quantity of liquid material and in some embodiments displays and stores information pertaining to the quantity of such liquid material for later review by medical staff personnel.

In accordance with another aspect, the present invention involves a suitable wall-mounted vacuum port connected to a central vacuum. Connected to the vacuum line is a collection vessel in which fluids are collected and fluid quantities and weights are measured and the data stored. The collection vessel may be reusable or disposable. In the instance of reusable containers and connectors and/or filter units, the canister, connector and/or filter units are decontaminated before a subsequent use.

In a further embodiment, the device is permanently installed within the wall structure of the facility, operably coupled to the existing facility's wall suction system and directly connected to both the facility's electrical system and sanitary sewage systems.

The device can be installed in the facility's ceiling structure, utilizing installed suction and electrical components of said facility or devices while incorporating a pumping system for removing the waste fluid from the site of the medical procedure. In the event a suction line is not readily accessible in the facility, the device of the present invention may employ its own internal source of suction such as a vacuum pump.

In accordance with a still further embodiment, the device may be portable, e.g. mounted on wheels or other suitable means of propulsion and with secure or permanent connection to a suction source, electrical components and sewer drainage system. This will provide for maximum flexibility in positioning the device within the procedural setting. For example, the device of the present invention may be modified for installation and/or deployment in portable procedural sites, e.g. ambulances, medical transports, portable surgery centers and/or other free standing procedural settings. An additional feature of the invention is remote control activation and control by means of a touch or voice-activated mechanism to control and regulate suction and measurement capabilities.

It is a further feature of the invention that the connector structure includes more than one inlet, whereby more than one end effector may be coupled to the central vacuum system. Flow rates or vacuum pressures with respect to each of the inlets may be displayed and controlled separately to provide for different degrees of suction on plural lines.

As a further aspect of the invention, certain features within the device will alert healthcare workers if the pressure within the system falls below predetermined levels established by the hospital or other medical facility. Parameters for pressure display, alerts, and alarm functions may be programmed into the system using the electrical or microprocessor based components installed into the device.

The connector used may comprise a body having an inlet side and an outlet side. The outlet side is suitably adapted to be coupled to a typical vacuum port on the housing and the inlet side is adapted to operably receive or be coupled to one or more end effectors or to conduit structures leading to end effectors. Any suitable coupling or connection methods may be used including "quick-release"—type connectors, Luer type, detent-type connectors, screw-type connectors or bayonet connective structures. Additionally, suitable coupling of conduits and the connector of the present invention may be accomplished by simple friction fitting.

The receptacle of the present invention may comprise a molded bottle-like container for holding a liquid and/or gaseous media and may provide for the separation of liquid from gaseous material, yet involve a single suction source suitable for moving and collecting both liquid and gaseous material within the container module.

The receptacle may also include an anti-siphon mechanism, such as a flapper check valve, to prevent retrograde or reverse flow of the liquid contents of the system to the procedure site should the suction system malfunction or the device suffer some other form of malfunction.

In some embodiments, a chemical separator or other non-mechanical separation method may be used. For example, a suitable media may be disposed in or adjacent to the ports of the connector.

In accordance with yet another aspect of the invention, within the body of the connector, there is a separating structure comprising a mechanical device for separating out liquid as the gas/liquid combination flows through the separation chamber. The separation chamber may include a suitable fluid counter, flow meter or monitor for measuring the quantity of the liquid passing into and/or through the baffle, separation mechanism, or trap. Both the original liquid/gas combination picked up from an operating site and the liquid separated from the gas/liquid material are moved by vacuum generated by a suction system and are pulled into the inlet port of said suction system. Alternately, a pump or other means may be used to move the gas/liquid material. Every conduit portion or gas/liquid flow path in the connector may have a separate liquid/gas separator structure, or they may share one common separator structure.

The receptacle may also include separation devices that employ a dual chamber to isolate and deturbulate the mixture of gas and liquid in a holding chamber, and may incorporate screen filters and meshes to further promote gas and liquid separation. It is contemplated that the separation of gas from fluid may incorporate a deflector, trap or other suitable device, e.g. a baffle, filter, etc. for optimizing the separation of liquid and gaseous material. A liquid measuring capability may be incorporated into the main-line vacuum portion, i.e., in the wall of the operating room, between the connector of the present invention and the inlet port, adjacent to the inlet port, or in the central mechanical room.

A gas permeable, but liquid impervious, filtering media is used to prevent inadvertent flow of liquid into the vacuum system. The filtering media is accessible for replacement or cleaning. The filter mechanism may incorporate sensors to inform healthcare personnel when and if its function is impaired or compromised.

The apparatus has a holding reservoir with an inlet side and an outlet side. The outlet side incorporates a valve type mechanism, e.g., a solenoid valve that retains the fluid in said reservoir until it is opened to allow flow of fluids into the measurement chamber. The holding reservoir is preferably positioned within the device housing in a manner that permits its contents to be viewed by the healthcare team at any time.

The system further comprises a measurement chamber having an inflow and an outflow path. Both paths are controlled by a valving mechanism, e.g., solenoid valves, which work in conjunction with and at the direction of a programmed microprocessor. During the measurement cycle, the outflow (lower) solenoid valve is in the closed position and the top solenoid valve is opened, permitting flow of fluids into the measurement chamber. When a sensor, e.g., a ball-type float, detects that a predetermined amount of fluid is within the chamber, the upper solenoid valve closes and a measurement is initiated.

The recorded measurement is a function of the capacity of the measurement chamber after the sensor closes the upper solenoid. When the amount of the fluid within said measurement chamber is calculated, the volume measured is transmitted to a microprocessor and the data is summed with the previously measured volumes and displayed for the medical staff as noted previously, on the face plate of the device, or at a site remote from the device. Alternatively, the measurement may be a flow of fluid of a known density through a sensor utilizing one of various forms of measurement, e.g., infrared sensor, as a means to determine volume. Separated fluids are measured for volume by passing into a measurement container of a known volume through a valve switching system that may include, but not be limited to, a solenoid valve.

Alternatively, the fluids may be removed from the container by a pump, such as a peristaltic pump, where volumes of fluid removed by said pump may be calculated, using such parameters as the number of revolutions of the pump rotor coupled with internal tubing capacity of said pump. As fluid passes through the peristaltic pump, each revolution has been calibrated in a manner that permits a volume value in milliliters to be associated with each revolution. As each revolution is counted, that volume value is transmitted to a display on the front of the panel, updating the volume reading. At the conclusion of the surgery, the value can be transferred to a paper record on the patient's chart and balanced with the input amounts of fluid to insure that no excess fluids have been left in the body cavity and that no excessive fluid loss that cannot be identified has occurred.

It is contemplated that fluids can be measured alternatively by monitoring and recording pump run time, weight of liquid, or direct volume measurement by use of flow metering.

The fluid volume measurements are preferably stored within a central storage mechanism, such as a microprocessor, and total fluid volumes stored during a given procedure are tabulated and displayed on the faceplate of the unit. These volume measurements may be stored and displayed at other sites within the facility or they may be transmitted to outside storage sites. The data transmission methods may include hard wiring through the facility's electrical or telecommunication lines, or via a form of wireless transmission or other acceptable means of conveying data. These values can be displayed as a trend line—time versus volumes removed.

In accordance with a further feature, the separated fluids can be retained in a holding chamber utilizing a valve system, e.g., a solenoid switch, to contain the fluids until they are processed through the measuring chamber or until such time as an alternate measuring method is completed and data is transmitted to the microprocessor. The measurement criteria may include other parameters, e.g., weight of the fluid. Here, the measurement container may be suspended from a load cell or strain gauge and produces an output proportional to weight. The system of the present invention may include an input feature, such as key-pad counter, touch screen or the like whereby the quantity of liquid brought into the device from the procedure site is measured, stored and/or displayed, and wherein a known quantity of liquid, e.g. saline, anesthesia materials, etc., may be inputted into the device. In this embodiment, a calculation feature, e.g., a microprocessor, calculator or the like, is provided whereby the quantity of input liquid may be subtracted from the total displayed volume to calculate, for example, blood loss or saline use during a surgical procedure. Other calculations may be performed as well, such as calculation of flow rates or weight of the material so removed and measured.

Alternatively, the device may accept the use of a docking station to allow the use of an existing CPU computer and input devices, including touch screen and personal data equipment, that can function in a stand alone or networked capacity. It is anticipated that printout capacity will be available, and data can be recorded and stored for further processing and use.

The remote device mentioned above may store and display data pertaining to volumes of fluid collected, volume of fluid introduced, total estimated blood loss, weight of fluid collected, weight of fluid introduced and other pertinent information including, but not limited to, system pressure values, trend line analysis, calculation and alarms. It is also contemplated that the remote device may have a camera that permits the remote monitoring of fluid color within the holding reservoir.

Fluid from the measuring chamber is discharged into the sanitary sewer by opening a valve, e.g. solenoid valve, at the outflow side of said chamber following measurement of the fluid volume within said chamber and transmission of the data to the microprocessor. A pressure relief valve provides for the venting of ambient air to allow more rapid emptying of said reservoir.

In an additional embodiment, a device which has a holding reservoir with and inlet side and an outlet side, and a separate sensing reservoir in which sensors are positioned such that the activation of an electronic sensor element results in a pump activating or deactivating to control the level of the fluid within the reservoirs. The reservoirs are connected by a tube or other conveyance such that levels within said reservoirs remain equal. When the high level sensor is activated, fluid is pumped from the reservoirs to the drain tube and is measured as it passes through the pump. When the fluid level drops below the lower sensor, the pump is hut off. This process repeats itself throughout the procedure with the resulting volume of fluid pumped from the reservoirs being continuously tabulated and displayed on the faceplate of the said device.

In one embodiment, the device has a sensor within the holding reservoir that activates the pump when an overflow situation occurs. Said holding reservoir contains a mesh screen located just below the overflow sensor that captures and neutralizes any foam created by the turbulence of the fluid entering the holding reservoir.

In accordance with another aspect of the invention, information pertinent to fluids introduced during a procedure may be incorporated and stored using automatic features e.g. bar code reading of saline solution packaging.

A cleaning fluid may also be injected into the chamber for cleaning the chamber after the lower solenoid valve is actuated to release its contents, thus preparing said chamber for the next measurement cycle. Once the flushing operation is completed, the lower solenoid valve closes and the next measurement can be performed. The cleaning kit may provide for post-procedural decontamination of the internal surfaces of the system. The cleaning solution may be stored within the device housing or may be applied externally, via a suction port. The storage container may be disposable or refillable and contain a premixed concentration of cleaning and disinfecting solution. For example, the decontamination unit may take the form of a plastic container, which contains a premeasured amount of a decontaminating, disinfecting, sterilizing or cleaning solution. In one embodiment the decontamination unit is adapted to be attached to the filter box or to the connector, and the contents are then withdrawn from the container upon actuation of the vacuum source. Once emptied, the container may be disposed of and the system is ready for its next use. The decontamination unit may also include a flow regulating mechanism or structure, and or decontaminates may be loaded or contained in separate compartments whereby they may be dispensed together, selectively or sequentially.

The cleaning solution container may contain a concentrated solution that is mixed with water drawn from the facilities water supply or from an alternate water or saline source. Further, the amount of solution in the container may be displayed for healthcare personnel to monitor.

The cleaning solution may be introduced into the separation chamber to permit cleaning of all interior surfaces following completion of the procedure, or alternatively, it can be introduced into the measuring chamber as a means to flush and clean the chamber on a continuous basis during the procedure.

In the preferred embodiment, the display may also include warnings, alarms and other means of notifying healthcare personnel of malfunctions, low fluid levels within the canister or other parameters to be identified.

The system and method of the present invention may be used in situations and applications other than the medical field. For example, in certain industries and manufacturing processes, washes or flows of fluids, are used for cooling and lubricating while a particular procedure is carried out. In these situations, it may be desirable to contain, control or manage the flow of cooling or lubricating material and to measure the quantity of the liquid being used and/or being consumed by the process. Similarly, potential hazardous and infectious materials in other markets, including but not limited to veterinary medicine, research facilities, manufacturing and industrial applications, coroner and mortuary procedures, and food processing applications, present opportunities for additional applications of the invention in all its embodiments.

Other features and advantages of the invention will become apparent from the following detailed description of a preferred embodiment, especially when considered in conjunction with the accompanying drawings in which like numerals in the several views refer to corresponding parts.

DETAILED DESCRIPTION OF THE EMBODIMENTS

With regard to fastening, mounting, attaching or connecting components of the system of the present invention to form the connector or the system, as a whole, unless specifically described otherwise, such are intended to encompass conventional fasteners such as screws, nut and bolt connectors, snap rings, clamps, such as hose clamps, screw clamps and the like, rivets, toggles, pins and the like. Components may also be connected or coupled by welding, friction fitting or deformation. Electrical components and connections may be made using appropriate electrical components and connection methods including conventional components and connectors, suitable display devices such as digital or analog devices, LED's or other light sources and the like and suitable microprocessor or integrated electrical components. Measuring devices, such as flow meters, sensors transducers and the like for measuring volume, flow rate, weight, or liquid quantities, may be selected from such measuring devices which are suitable for use in the present invention. Unless otherwise specifically disclosed or taught, materials for making components of the present invention may be selected from appropriate materials such as metal, metal alloys, fibers, plastics, and the like, and appropriate manufacturing and/or production methods including methods including casting, extruding, molding and machining may be used.

Figure 1:
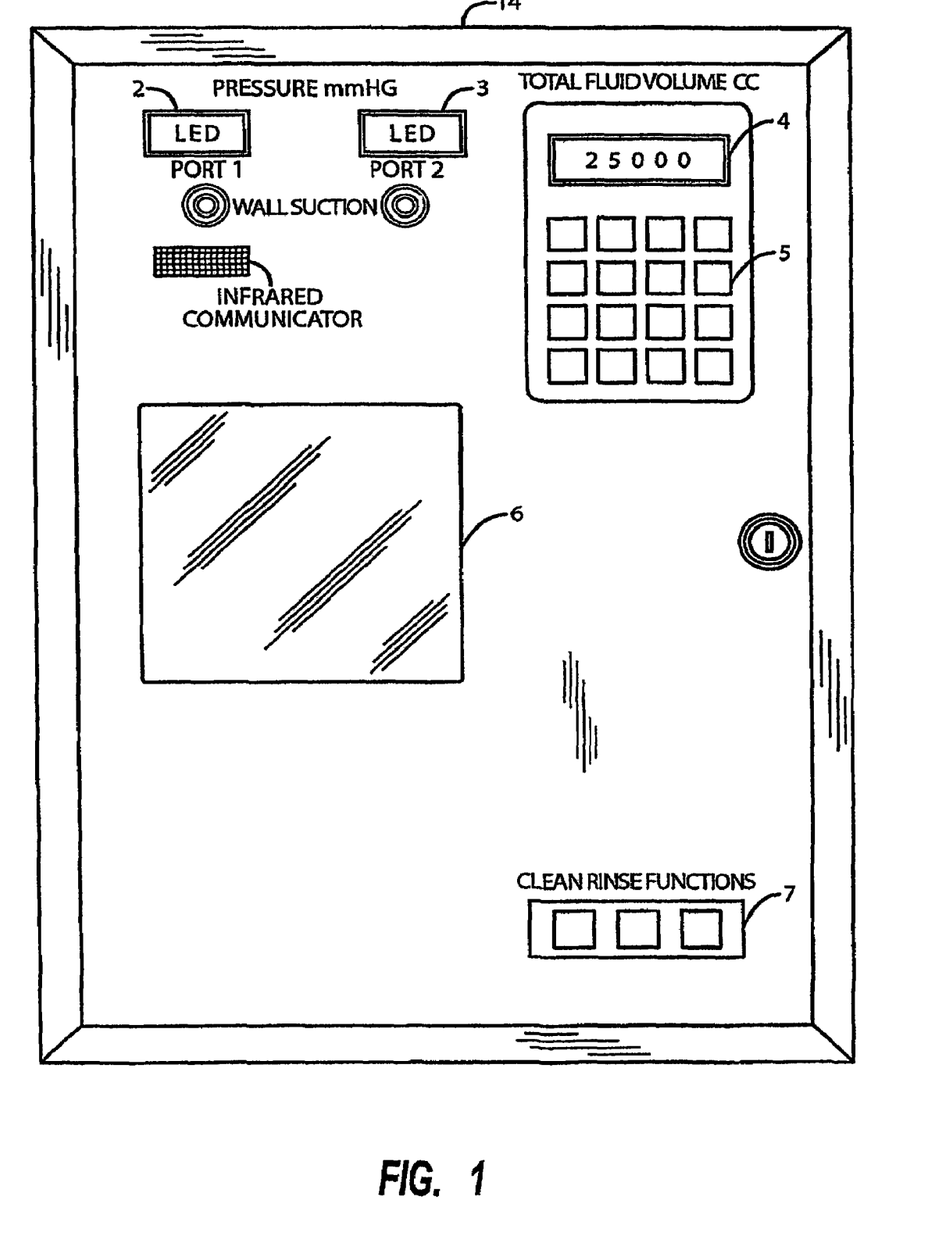
FIG. 1 is a frontal view of the face panel of the device comprising a preferred embodiment of the invention.

As shown in FIG. 1, the present invention relates to a liquid collection, measurement and automatic disposal device for use in various surgical and post-operative situations where potentially infectious waste must be removed from the patient environment, collected and measured for quantity of fluid, providing for methods of calculating certain aspects of hemostasis, and disposing of said fluid automatically with minimal contact by the healthcare team. In one embodiment, the present invention comprises a system enclosed within a box-like housing 14 where fluids from the patient are collected by an end effector (not shown) coupled by tubing to a vacuum source connected to suction port 1. The suction source may be installed within the unit or may rely upon existing suction sources. Fluid and gaseous matter is separated within the unit 14 and the retained fluid is held, measured and data relating to volume collected is stored prior to disposal. In the embodiment shown, such a system may include a pair of inlet ports, here labeled port 1 and port 2. A pressure display 2 and 3 is provided for each port. Also, a fluid quantity display 4, a keypad 5 for calculation, a fluid viewing port 6 and accessory control panel 7 are built into the housing unit 14.

Figure 2:
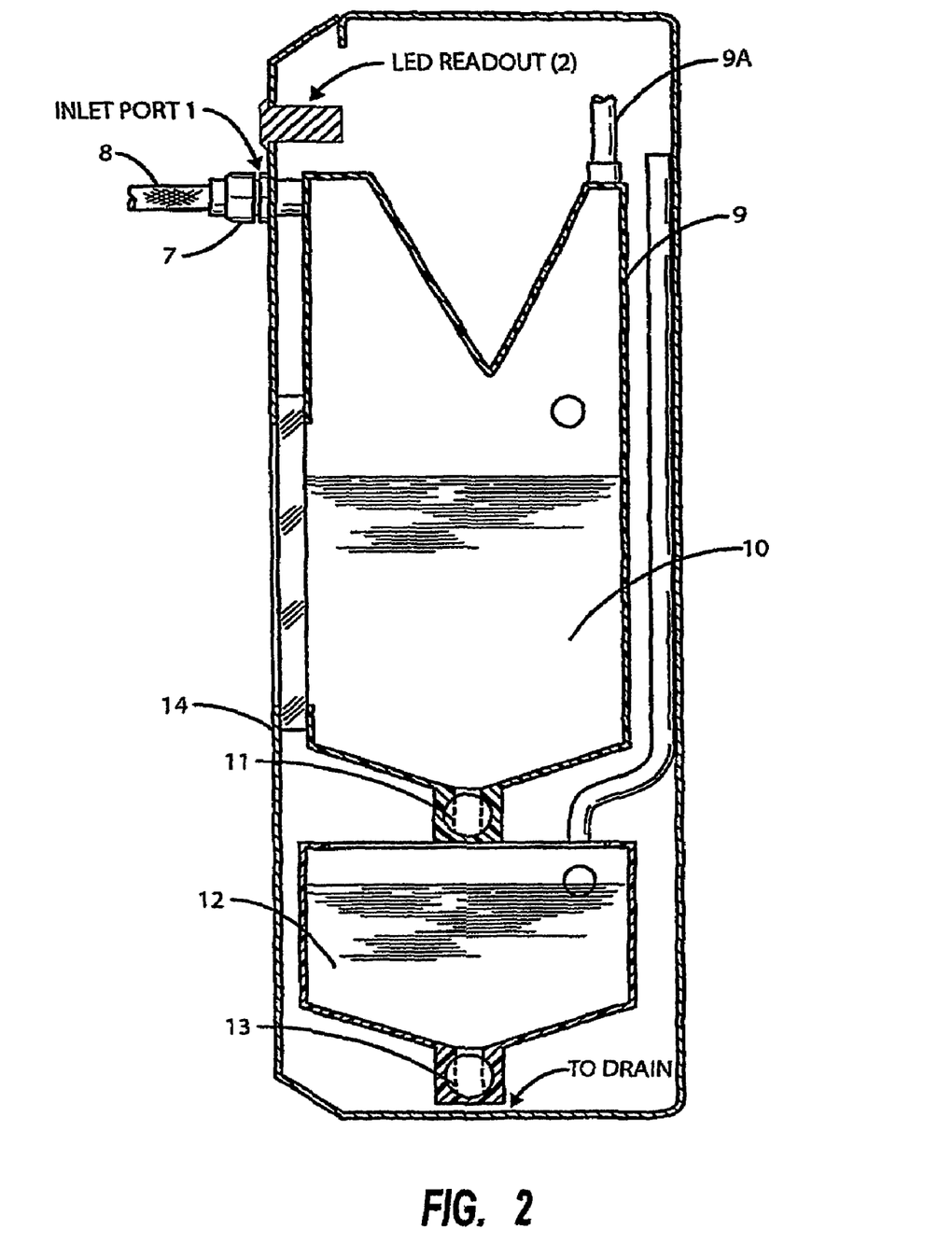
FIG. 2 shows a cross-sectional view of the device showing the internal structures located inside the wall of the device.

As shown in FIG. 2, fluid and gaseous waste from the wound site are suctioned into an inlet port 1 that is operably coupled to the wound site by a luer type lock 7 that is operably attached to tubing 8 leading to the wound site and through which the fluid and gaseous matter is collected. The fluid passes through a separation chamber 9 and the liquid component is deposited in a holding chamber 10. Gases are evacuated through a suction line 9A while liquid accumulates in holding chamber 10. When the measurement cycle begins, the holding chamber 10 empties its contents into the measurement chamber 12, via solenoid valve 11, until the capacity of the chamber 12 is reached, causing the upper solenoid valve 11 to close. The measurement chamber 12 performs its measurement, sending the data to the display 2 (FIG. 1) and storing the information within the memory of the calculator 4. Once the measurement is completed, the lower solenoid valve 13 opens and the measurement chamber empties its contents via a tube (not shown) directly to the sanitary sewer. Once emptied, the lower solenoid valve 13 closes and the upper solenoid valve 11 reopens, initiating another measurement cycle. This cycle is repeated automatically until the medical staff concludes the procedure or terminates the measuring cycle.

Figure 2A:
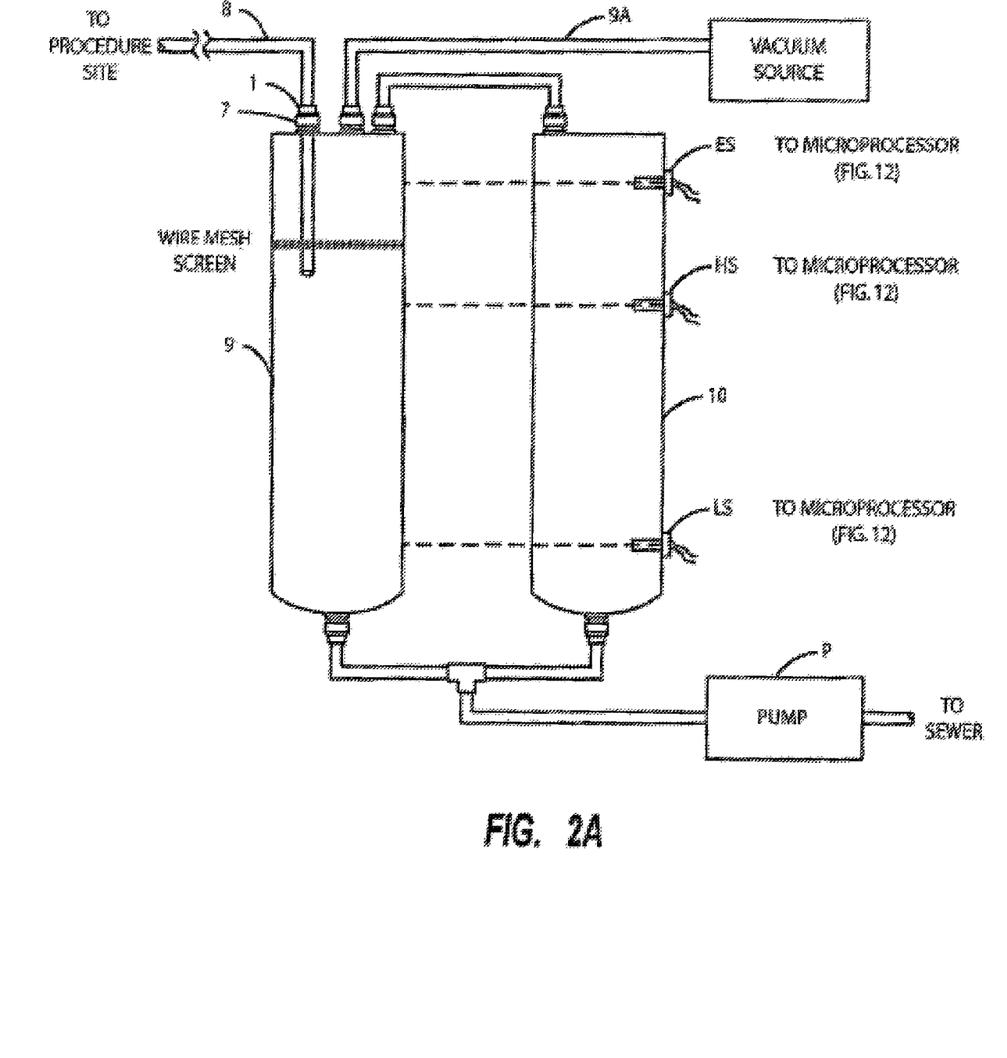
FIG. 2A shows an alternative embodiment of the apparatus of FIG. 2.

As shown in FIG. 2A, fluid and gaseous waste from the wound site is suctioned into an inlet port 1 that is operably coupled to the wound site by a luer type lock 7 which is operably attached to tubing 8, which extends to the wound sites and through which the fluid and gaseous matter is collected. The fluid passes through a separation chamber 9 and the fluid is deposited in a holding chamber 10. Gases are evacuated through a suction line 9A while liquid accumulates in holding chamber 10. When the liquid level reaches the high level sensor HS, the measurement cycle begins. A pump P starts and empties the reservoir 10 until the low level sensor LS is reached, causing the pump P to stop. An emergency sensor ES is provided to shut down the suction line 9A in the event that the pump fails to turn on when the high level point is reached. This prevents liquid from being sucked into the vacuum line. The measurement is accomplished by multiplying the pump run time by the volume movement capacity per second of the pump. This data is sent to the display 2 (FIG. 1), which visually presents the data accumulated and store within the memory of the calculator 4. This cycle is completed automatically until the medical staff concludes the procedure or terminates the measuring cycle.

Figure 3:
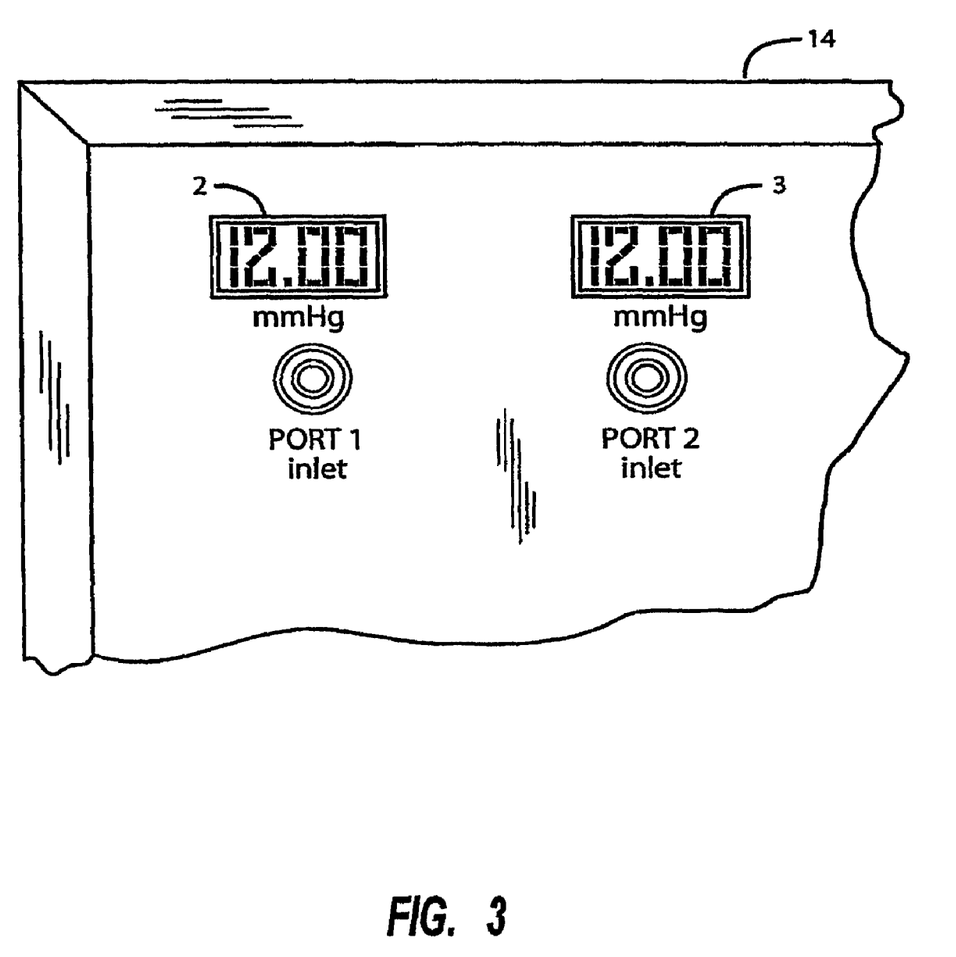
FIG. 3 is a close-up view of the inlet ports and pressure gauge displays shown in FIG. 1.

FIG. 3 depicts the pressure gauge display panels 2 and 3, which provide information pertaining to the ambient pressure drop within the system, measured in millimeters of mercury or other suitable units. Such pressure drop information is important to surgical personnel to assure that adequate suction is available for fluid transfer and that no potential exists for reverse flow that would compromise the wound site and the healthcare team. In the exemplary embodiment, a pressure status is indicated by a liquid crystal or LED digital display. Alternatively, pressure status can be provided by a colored light or by an audible beep. This alarm function is programmable using the keypad 5 (FIG. 1).

Figure 4:
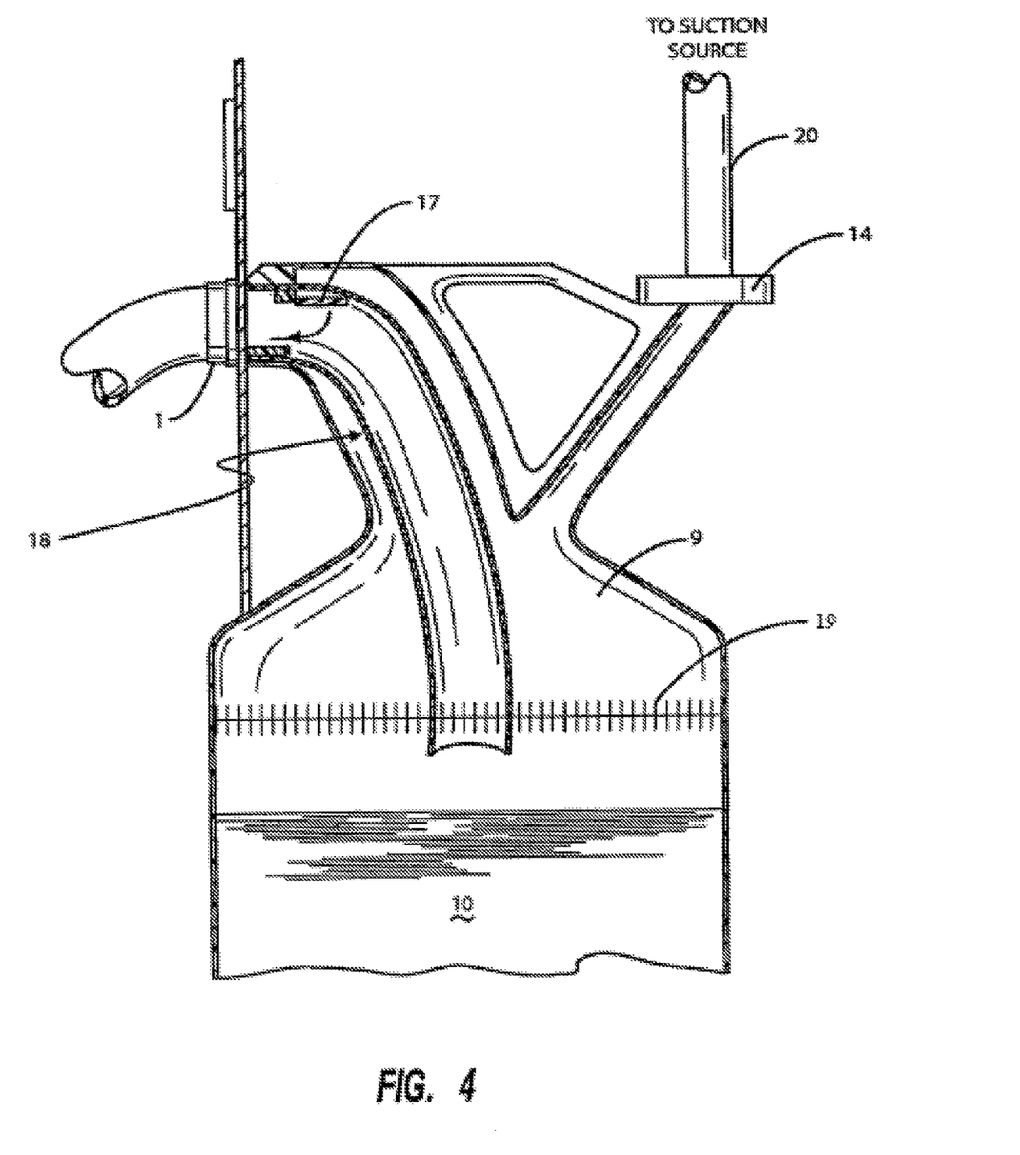
FIG. 4 is a close-up view of the inlet ports and pressure gauge displays shown in FIG. 1.

FIG. 4 depicts the flow of fluid and gaseous matter through the separation chamber 9. Waste fluid and gas is received through the inlet port 1 that is fitted with an anti-siphon valve 17 to prevent inadvertent back-flow of fluid and gas to the fluid collection site. The gas and fluid mixture is separated by baffle mechanism 18 with the fluid dropping into the holding chamber 10 and the gas traveling upward through a filter mechanism 19 which is designed to prevent inadvertent egress of liquid in the primary suction line 20 that is connected to the hospital suction system or in one embodiment its own independent suction source.

Alternatively, in FIG. 4, a foam suppressor is provided. The fluid enters in to the primary chamber 9 below a screen mesh foam separator 9'. As mentioned, waste fluid and gas is received through the inlet port 1 that is fitted with an anti-siphon valve 17 to prevent inadvertent back-flow of fluid and gas to the fluid collection site. The secondary chamber is connected to the primary chamber in such a way as to allow for free and balanced flow of liquids between the chambers while limiting the presence of foam in the secondary chamber 10.

Figure 5:
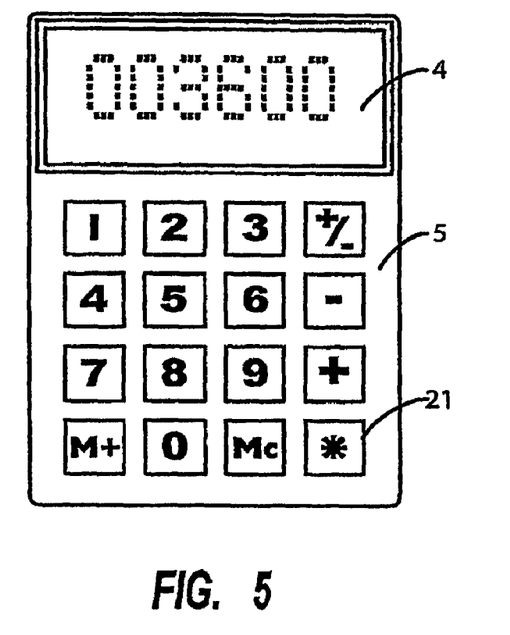
FIG. 5 is a close-up view of the fluid volume display and calculation function.

FIG. 5 is a close up view of the fluid quantity function 4 of FIG. 1 and the keypad 5. The fluid display registers the amount of fluid that has been measured in the measurement chamber and disposed of into the sanitary sewer. The numeric keypad has a number of uses, including calculating final estimates of blood loss, and other features that may be accessed through the function keys 21. Other data may be stored using a function key as well. For example, fluid added to the surgical field may be inputted to the computer display panel 4, allowing for automatic calculation of fluid loss which decreases the potential for human error in addition/subtraction. It is further contemplated that a hard copy printer (not shown) be provided to produce documentation for a patient's chart. Real-time input capabilities, either manual or via a bar code reader, permit the surgical team to estimate blood loss or fluid retention during the course of the surgical procedure rather than at the end thereof.

Figure 6:
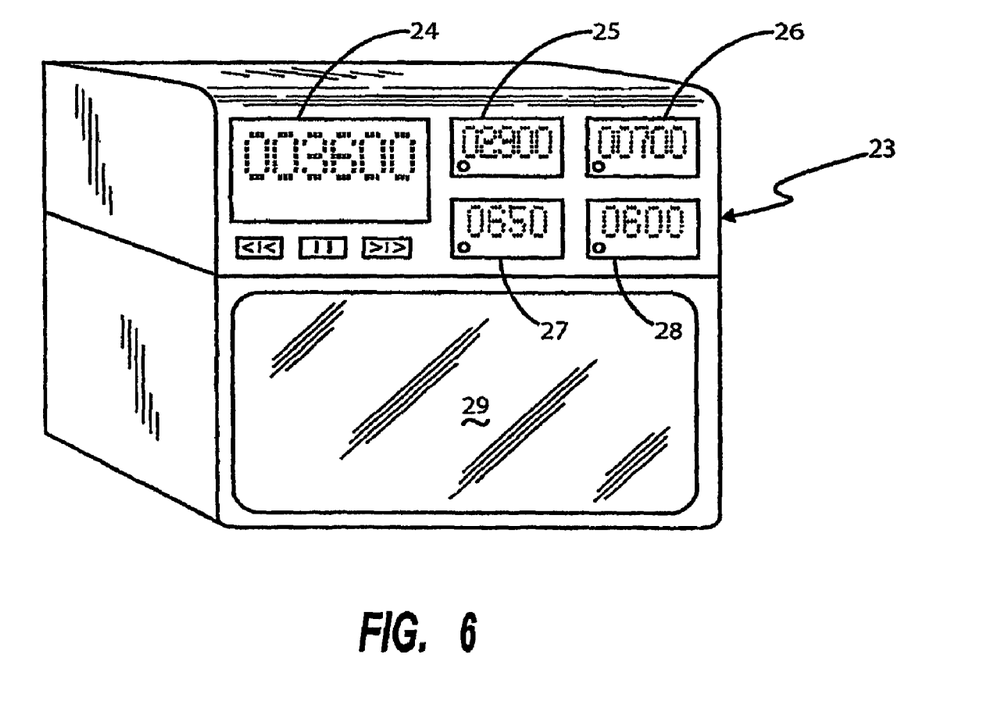
FIG. 6 is an embodiment of a remote instrument that stores and displays information pertaining to fluid volume withdrawn form the site, fluid volumes introduced, estimated fluid loss, weight of fluid withdrawn and a weight reference point for assessing the density of the material suctioned.

FIG. 6 depicts one embodiment of a remote instrument 23 that provides information pertaining to the current status of the total fluid volume removed from the wound site at display 24, the amount of fluid that has been introduced into the surgical field at display 25 and an estimated fluid loss calculation at display 26. The instrument may also include a display depicting the actual weight of the fluid removed from the wound site via display 27 and the estimated weight of said fluid if it were composed of 100% saline irrigation at display 28. These depictions may contain important clinical information to the surgical team pertaining to the nature and make-up of the fluid being removed from the wound. The remote instrument may also display information pertaining to the ambient pressure within the suction system, including, but not limited to, actual pressure, warning displays and alarms. A wireless communication link may connect the unit in the operating room to the remote device 23. This device may provide real-time data on suction fields, as well as providing a function display that shows inputted fluid volumes and estimated fluid loss, allowing an anesthesiologist or personnel at a remote monitoring site to be alerted to changes in fluid balance and to determine whether other vital signs are abnormal. The instrument 23 may also incorporate a touch screen 29 as a data input means.

Figure 7:
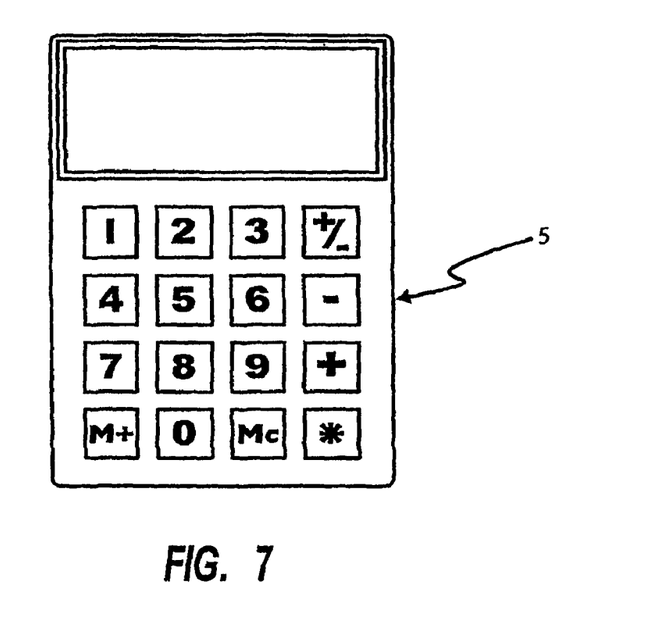
FIG. 7 is a rendering demonstrating fluid loss calculation.
Figure 8:
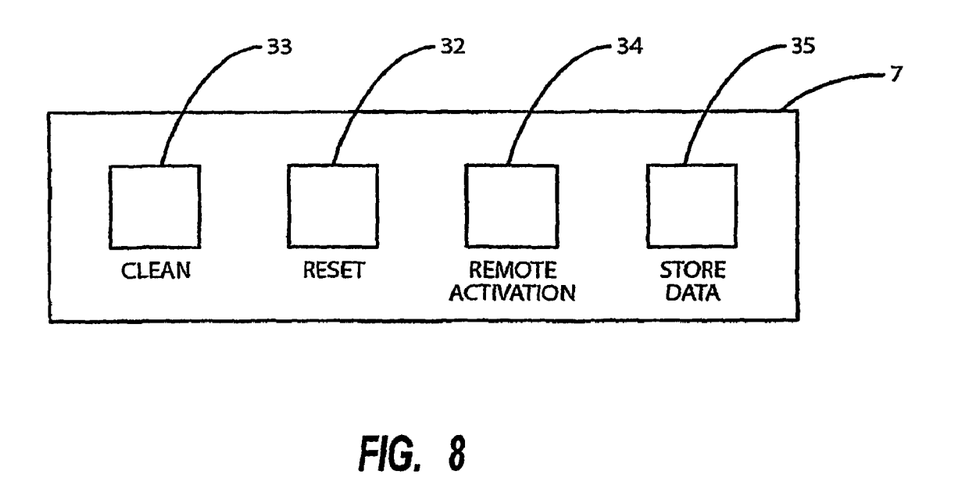
FIG. 8 illustrates an accessory panel with such features as an On/Off control, Cleaning Cycle control, Remote Activation Control and Data Storage Command.

In FIG. 7 is depicted a calculator for calculating estimated fluid loss. At the conclusion of the procedure, a healthcare professional keys the volume of introduced fluids into the keypad 5, using a keypad function. Once the introduced fluid is entered, additional calculations can be entered through the keypad to factor in blood and fluids retained by absorbed materials. Once all introduced and adjusted calculations have been made, the keypad is activated and an estimated blood loss is calculated and stored in the calculator's memory for the operative report. It is also contemplated that the display screen of the calculator 5 have a touch screen capability, adding further input capabilities than is afforded by the keyboard In FIG. 8 is depicted a further embodiment of the accessory panel 7. It provides the operator with selection choices for such ancillary functions as On/Off (push button 32), Cleaning (push button 33), Remote Activation Control (push button 34), and Data Storage Command 35. These are representative features and are neither exclusive nor limiting. Other features may be added or substituted as determined by technological advances, regulations or customer needs.

Figure 9:
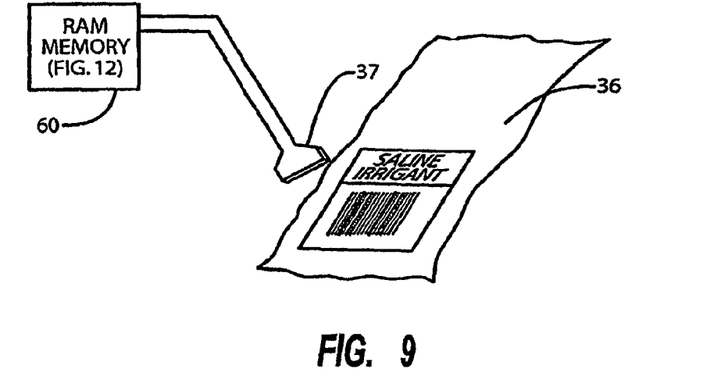
FIG. 9 is a view of a possible bar code reading function.

FIG. 9 depicts one embodiment of a method for automatically entering and storing information pertaining to fluids being introduced to the wound site from an outside source. The saline solution package 36 has a bar code that is scanned by a bar code reader 37 that is operably coupled to the data storage module 60 of the system. The volume of the saline and possibly other information may be automatically factored into the final blood loss calculation and may also be forwarded to other departments in the facility for purposes of data collection and analysis and inventory management.

Figure 10:
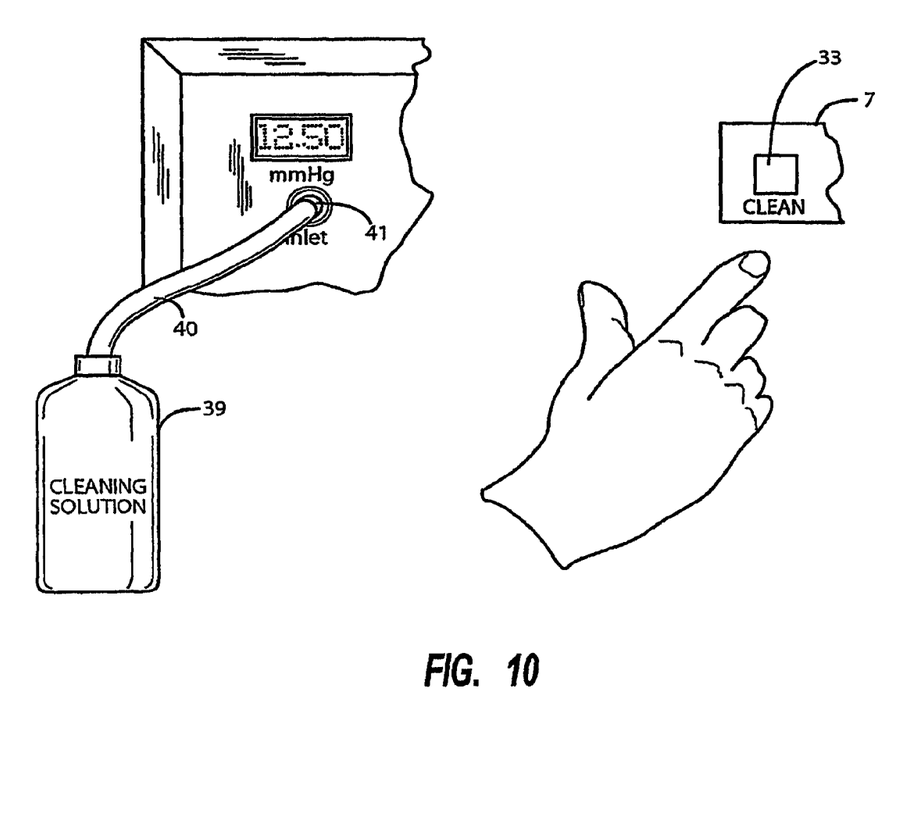
FIG. 10 illustrates a Cleaning Cycle procedure using a separate canister.

FIG. 10 is intended to illustrate additional hardware for implementing a cleaning cycle for the system to be used at the completion of the service cycle. The cleaning solution kit consists of a bottle 39 containing a predetermined volume of liquid cleaning solution, a tube 40 and luer connector 41 for coupling the assembly to the inlet port 1 (FIG. 1) by engaging the luer connector 41. The operator activates the cleaning cycle by depressing the cleaning cycle switch 33. Fluid is suctioned from the bottle 39 and passes through the valves and chambers shown in FIG. 2 before passing to the sanitary sewer. Once the cycle is completed the luer connector 41 will be disconnected from the inlet port and the cleaning solution kit is disposed of as biohazardous waste.

Figure 11:
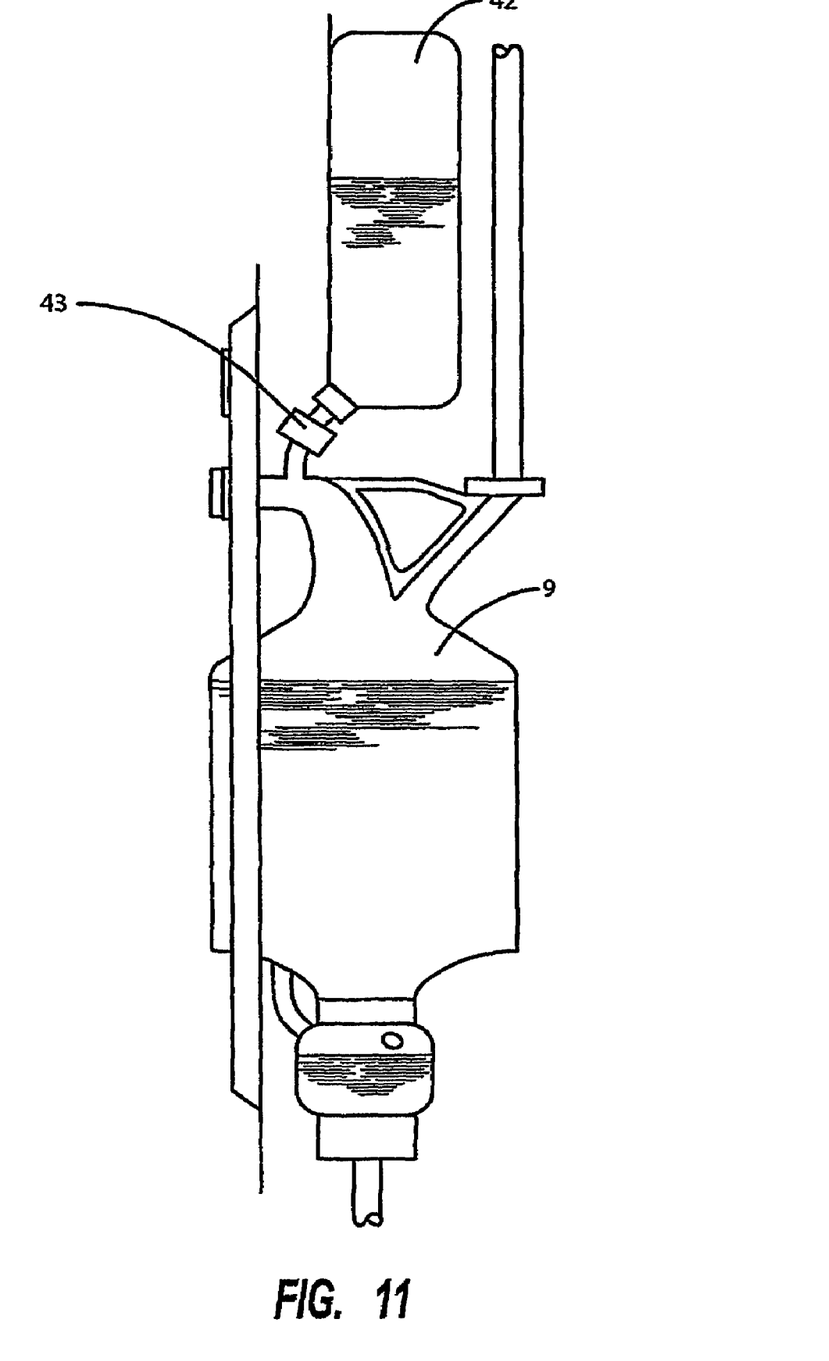
FIG. 11 shows an internal cleaning solution storage canister that can drain through the separation chamber or directly into the measurement chamber.

In FIG. 11 is depicted an alternative embodiment where cleaning solution is stored in a container 42 within the device housing 14 adjacent to separation chamber 9. When the operator activates the Cleaning cycle, a predetermined volume of the cleaning solution enters the device through a solenoid valve 43 at the separation chamber 9, cleaning the instrument for the next use. An alternative embodiment provides for continuous cleaning of the device during the procedure with those quantities being stored for later analysis and comparison to estimated blood loss. In this embodiment, actual amounts of cleaning solution used may be displayed one the front panel of the device housing 14.

Figure 12:
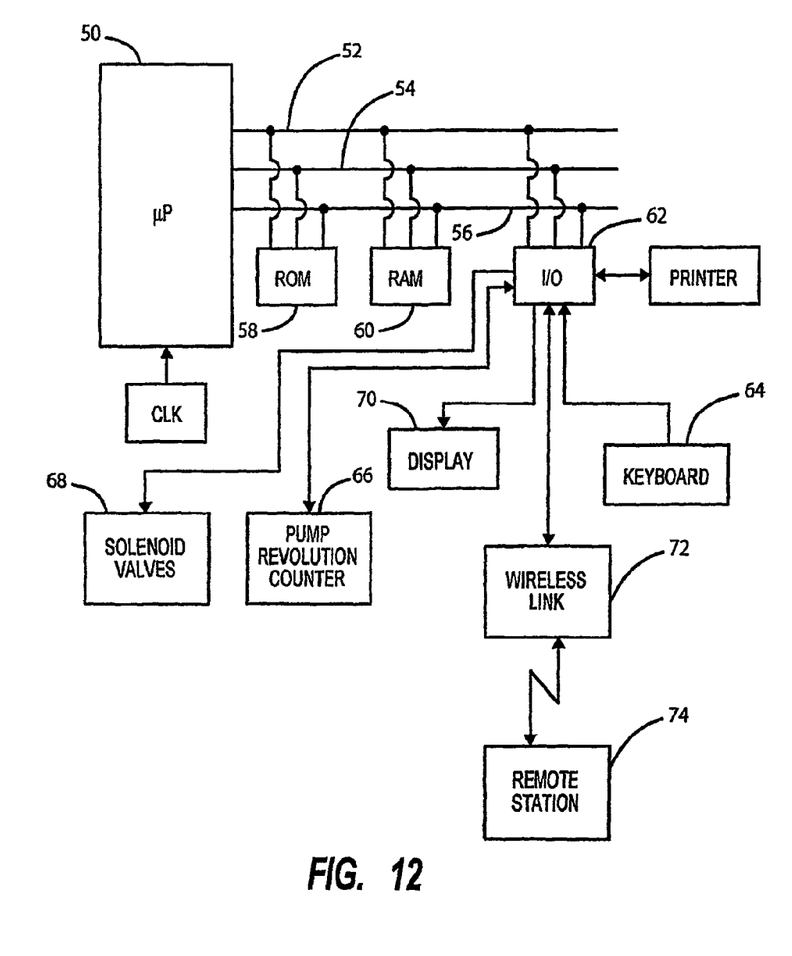
FIG. 12 is a schematic diagram of the electronic controller used in the system.

FIG. 12 is a schematic diagram of the control module for the system of the present invention. It is seen to include a microprocessor 50 having an address bus 52, a data bus 54 and a control bus 56 connecting it to a ROM memory 58, a RAM memory 60 and an input/output (I/O) interface 62. The microprocessor 50 is adapted to receive manual inputs from a keyboard 64, via the I/O module 62 as well as signal inputs from a peristaltic pump revolution counter 66. Thus, depending upon the type of volume measurement system incorporated, the volume information will be either manually entered, via the keyboard or automatically entered from the pump revolution counter 66.

Under control of a program stored in the ROM memory 58, the microprocessor will control the solenoid valves 11 and 13 (FIG. 2) to first transfer fluid from the chamber 9 to the measuring/weighing chamber 12 and for subsequently emptying the weighing chamber 12 once the appropriate measurements have been derived. In the case of the embodiment of FIG. 2A, the microprocessor will receive inputs from the level sensors LS and HS and ES to control the on/off state of the pump P and will accumulate liquid flow data from the pump revolutions or from a flow meter disposed in the line leading to a sanitary sewer.

The displays 2 and 3 shown in FIG. 3 as well as the display 4 in FIG. 4 receive information from the microprocessor 50, via I/O module 62, as indicated by the block 70 in the schematic drawing of FIG. 12.

The remote instrument illustrated in FIG. 6 is coupled by way of a wireless link 72 to the I/O interface 62 whereby data computed and entered into the RAM memory 60 may be transferred to the remote station 74. Moreover, data originating at the remote station 74 may be transferred via the wireless link 72 to the microprocessor 50.

Since the computations needed to operate the system of the present invention involve only simple mathematical operations of addition, subtraction and multiplication, the software program executed by the microprocessor 50 can readily be perceived by those skilled in the art, obviating the need to set forth the source code herein.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A method for disposing of waste fluid, said method comprising the steps of:
   (a) drawing a volume of waste fluid from a waste fluid source into a chamber under negative pressure;
   (b) detecting when liquid waste of said waste fluid reaches a predetermined high liquid level volume in said chamber;
   (c) while maintaining said negative pressure in said chamber, a pump pumping said liquid waste from said chamber through a fluid outlet until said liquid waste reaches a predetermined low liquid level volume, said pump disposed between said chamber and said fluid outlet; and
   (d) measuring said liquid waste volume pumped through said fluid outlet.

2. The method of claim 1 wherein said chamber includes a separation chamber and a holding chamber, both under said negative pressure.

3. The method of claim 2 wherein said waste fluid is collected in said separation chamber and said liquid waste is separated into said holding chamber.

4. The method of claim 1 further including displaying said liquid waste volume pumped through said fluid outlet on a visual display.

5. The method of claim 1 further including disposing of said liquid waste pumped through said outlet directly into a sewer.

6. The method of claim 1 further including disposing of said liquid waste pumped through said outlet into a container.

7. The method of claim 1 further including monitoring said negative pressure in said chamber and displaying said negative pressure on said visual display.

8. The method of claim 1 wherein said waste fluid source is a surgical procedure site.

9. The method of claim 8 wherein said volume of waste fluid includes a bodily fluid volume and a saline volume collected from said surgical site, said saline having been applied to said surgical site from a saline source of known volume.

10. The method of claim 9 further including calculating and displaying said saline volume used during said surgical procedure.

11. The method of claim 10 further including calculating said bodily fluid volume collected in said chamber by subtracting said calculated saline volume from said liquid waste volume pumped through said fluid outlet.

\* \* \* \* \*